United States Patent [19]

Vaudry et al.

[11] Patent Number: 5,304,632
[45] Date of Patent: Apr. 19, 1994

[54] NEUROPEPTIDES OF THE TACHYKININ FAMILY

[75] Inventors: Hubert Vaudry, Mont-Saint-Aignan, France; J. Michael Conlon, Omaha, Nebr.

[73] Assignees: Creighton University, Omaha, Nebr.; Centre National De La Recherche Scientifique, Paris, France

[21] Appl. No.: 753,909

[22] Filed: Sep. 3, 1991

[30] Foreign Application Priority Data

Jun. 4, 1991 [FR] France ............................. 91 06759

[51] Int. Cl.$^5$ ..................... A61K 37/02; C07K 5/00; A23J 1/14; C07H 21/04
[52] U.S. Cl. ................................... 530/327; 530/314; 530/324; 530/387.1; 530/388.24; 536/22.1; 536/23.5
[58] Field of Search ............... 424/570; 530/350, 314, 530/327, 328, 334, 335, 324, 389.1, 388.1, 388.24, 324; 435/69.1, 252.3; 536/22.1, 23.5

[56] References Cited

PUBLICATIONS

Kozawa et al., "Isolation of Four Novel Techykinins From Frog (Rana catesbeiana) Brain and Intestine", Biochemical and Biophysical Research Communications, vol. 177, No. 1, (1991), pp. 588–595.

Emmett, "Tachykinin Receptors", Comprehensive Medicinal Chemistry, vol. 3 (1990), pp. 1001–1022.

Yashuhara et al., "The Studies on the Active Peptide on Smooth Muscle in the Skin of Rana rugosa, Thr$^6$--Bradykinin and its Analogous Peptide, Ranakinin-R$^1$", Chem. Pharm. Bull., vol. 7, No. 2, (1979), pp. 486–491.

*Primary Examiner*—Robert A. Wax
*Assistant Examiner*—Hyosuk Kim
*Attorney, Agent, or Firm*—Zarley, McKee, Thomte, Voorhees & Sease

[57] ABSTRACT

The invention relates to a peptide, characterized in that it corresponds to the following sequence of amino acids:

$$\text{Xaa}_1 \text{ Pro Xaa}_2 \text{ Pro Xaa}_3 \text{ Xaa}_4 \text{ Phe Tyr Gly Leu Met}$$

in which $a_n$ with n equal to 1, 2, 3 or 4 represents any amino acid, and in particular in that the peptide is ranakinin having the following formula:

$$\text{Lys Pro Asn Pro Glu Arg Phe Tyr Gly Leu Met}$$

The invention also relates to the use of this peptide in pharmacological applications.

7 Claims, 3 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: linear     ( i i ) MOLECULE TYPE: cDNA     ( i i i ) HYPOTHETICAL: NO     ( i v ) ANTI-SENSE: NO     ( v i ) ORIGINAL SOURCE:
        ( A ) ORGANISM: Rana ridibunda
        ( D ) DEVELOPMENTAL STAGE: Adult
        ( F ) TISSUE TYPE: Brain     ( i x ) FEATURE:
        ( A ) NAME/KEY: CDS
        ( B ) LOCATION: 1..33

( x i ) SEQUENCE DESCRIPTION: SEQ ID NO:1:

```
AARCCNAAYC  CNGARMGNUU  YUAYGGNYUN  AUG                    33
```

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( D ) TOPOLOGY: linear     ( i i ) MOLECULE TYPE: peptide     ( v ) FRAGMENT TYPE: N-terminal     ( v i ) ORIGINAL SOURCE:
        ( A ) ORGANISM: Rana ridibunda
        ( D ) DEVELOPMENTAL STAGE: adult
        ( F ) TISSUE TYPE: brain     ( i x ) FEATURE:
        ( A ) NAME/KEY: Peptide
        ( B ) LOCATION: 1
        ( D ) OTHER INFORMATION: /label=peptide
            / note="X in position 1 is a basic type amino
            acid, for example Arg, Glu, or Lys."

( i x ) FEATURE:
        ( A ) NAME/KEY: Peptide
        ( B ) LOCATION: 3
        ( D ) OTHER INFORMATION: /label=peptide
            / note="X in position 3 is Lys, Asx, or Asn."

(ix) FEATURE:
  (A) NAME/KEY: Peptide
  (B) LOCATION: 5
  (D) OTHER INFORMATION: /label=peptide
    /note="X in position 5 is Gln, Lys, or Arg."

(ix) FEATURE:
  (A) NAME/KEY: Peptide
  (B) LOCATION: 6
  (D) OTHER INFORMATION: /label=peptide
    /note="X in position 6 of the sequence is Gln, Lys, or Arg."

(xi) SEQUENCE DESCRIPTION: SEQ ID NO:2:

Xaa Pro Xaa Pro Xaa Xaa Phe Tyr Gly Leu Met
 1           5                        10

(2) INFORMATION FOR SEQ ID NO:3:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (v) FRAGMENT TYPE: C-terminal (vi) ORIGINAL SOURCE:
    (A) ORGANISM: Rana ridibunda
    (D) DEVELOPMENTAL STAGE: adult
    (F) TISSUE TYPE: brain (xi) SEQUENCE DESCRIPTION: SEQ ID NO:3:

Phe Xaa Gly Leu Met
 1             5

NEUROPEPTIDES OF THE TACHYKININ FAMILY

BACKGROUND OF THE INVENTION

Neuropeptides are very important messengers of nervous communication in animals. Among these neuropeptides, the tachykinin family, which contains multifunctional polypeptides exhibiting a structural homology in respect of their COOH-terminal portion, are known in particular. These polypeptides possess in common the following amino acid sequence at their COOH-terminal end:

Phe-Xaa-Gly-Leu-Met-NH$_2$ in which X is a variable aromatic or branched aliphatic amino acid.

Several polypeptides of the tachykinin family have been isolated and characterized to date, from frog skin (ERSPAMER et al. 1981, Trends Neurosci. 4, 267–269). Other studies have enabled several polypeptides of the tachykinin family to be isolated from different vertebrate species.

The tachykinins in amphibians may be grouped in sub-families established in accordance with the nature of the variable amino acid residue Xaa in the COOH-terminal region. Thus, the physalaemin sub-family in which Xaa in the formula given above is a tyrosine residue (Tyr), the eledoisin sub-family in which Xaa is an isoleucine residue (Ile) and the kassinin sub-family in which Xaa is a valine residue (Val) are known.

One particular tachykinin known independently of its presence in frogs is substance P described by CHANG and LEEMAN (J. Biol. Chem. 245, 4784–4790, 1970). Studies carried out to data in Rana esculenta frogs, and in particular on the brain of this frog, have demonstrated the presence of a nerve network in the brain of this frog by means of immuno-histochemical examinations employing antisera to substrate P (GAUDINO et al. 1980, Cell Tissue Res. 211, 241–250).

Another molecule of the tachykinin family is neurokinin B described by KANGAWA et al. (Biochem. Biophys. Res. Commun. 114, 533–540, 1983).

Despite the results obtained with antibodies directed towards substance P in frog's brain, the inventors of the present application have shown that substance P does not exist in frog's brain. On the other hand, the inventors have demonstrated and characterized a new peptide of the tachykinin family belonging to the physalaemin sub-family from the brain of the Rana ridibunda frog.

From this new peptide, referred to as ranakinin, they have defined a new group of peptides having in common an amino acid structure determined from the structure of ranakinin.

The invention also relates to the preparation of the peptides defined in the following pages, as well as to their use, for example, in pharmacological applications.

The peptides according to the invention are characterized in that they correspond to the following sequence of amino acids:

Xaa$_1$ Pro Xaa$_2$ Pro Xaa$_3$ Xaa$_4$ Phe Tyr Gly Leu Met in which Xaa$_n$ with n equal to 1,2,3 or 4, represents any amino acid.

The list of variable amino acids, Xaa$_n$, capable of participating in the composition of this peptide is presented below with the abbreviation corresponding to each amino acid in the form of the three-letter code.

| Amino acid | Three-letter code |
| --- | --- |
| Alanine | Ala |
| Arginine | Arg |
| Asparagine | Asn |
| Aspartic acid | Asp |
| Asparagine or aspartic acid | Asx |
| Cysteine | Cys |
| Glutamine | Gln |
| Glutamic acid | Glu |
| Glutamine or glutamic acid | Glx |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

According to a first particular embodiment of the invention, Xaa$_1$ is a basic type amino acid, for example arginine, glutamic acid and preferably lysine.

According to another particular embodiment of the invention, Xaa$_2$ is lysine, aspartic acid or preferably asparagine.

In another particular embodiment of the invention, Xaa$_3$ is glutamine, lysine or preferably arginine.

Advantageously, Xaa$_4$ may be selected from the following amino acids: glutamine, lysine or preferably arginine.

It is understood that the different subgroups of peptides defined by the choice of particular amino acids for Xaa$_1$, Xaa$_2$, Xaa$_3$ and Xaa$_4$ may be combined with one another, and consequently all such combinations between the different amino acids mentioned for Xaa$_1$, Xaa$_2$, Xaa$_3$ and Xaa$_4$ in the context of the amino acids sequence given above do form part of the invention.

An especially preferred peptide in the context of the implementation of the invention is that which corresponds to the following sequence of amino acids:

Lys Pro Asn Pro Glu Arg Phe Tyr Gly Leu Met

Advantageously, the above peptide skeleton is in amidated form at its COOH-terminal end, and corresponds in this case to ranakinin as isolated from Rana ridibunda frog brain.

In view of their membership of the tachykinin family, the peptides according to the invention, and especially ranakinin, are capable of involvement in vivo in the transmission of nociceptive information, but can also, like other tachykinins, be involved in blood pressure, inflammation, salivation, contraction of smooth muscle and the regulation of dopaminergic transmission in the nigrostriatal complex.

These functional interactions of tachykinins are carried out through binding to a receptor. The peptides according to the invention are capable of binding to receptors of the NK-1 type described by LAVIELLE et al. (Fondam. Clin. Pharmacol. 1990, 4, 257–268). They hence behave as NK-1 agonists.

According to a particular embodiment, the invention relates to a peptide as obtained of completion of the following steps:
  centrifugation of a frog brain tissue extract at 1600 g for 1 hour at 4° C.;

separation of the peptide fraction;

selection of the peptide fraction reacting with an antiserum in which the polyclonal or monoclonal antibodies recognise the COOH-terminal portion of substance P, this antiserum exhibiting, in addition, a reactivity of less than 0.5% with neurokinin A, neurokinin B and unamidated substance P;

purification by HPLC on a column equilibrated with an acetonitrile/water/trifluoroacetic acid (17.5/82.4/0.1, vol/vol/vol) mixture with a flow rate of 1.5 ml/min, the acetonitrile concentration in the elution solvent being raised to 31.5% during 60 min according to a linear gradient; and recovery of the peptide thus purified.

Different modifications of the peptide structure of the linkages of amino acids described above may be envisaged within the context of the invention. It is possible, in particular, to arrange to modify a peptide corresponding to one of the above formulae by removal of amino acids from its $NH_2$-terminal portion provided that the peptide thus formed retains its capacity to be recognized by antibodies directed towards ranakinin, and preferably remains protected against the aminopeptidases present in the cell environment when it is used in vitro or in vivo.

Also within the scope of the invention is a polypeptide containing a number of amino acid residues not exceeding 40, and preferably 30, characterized in that it comprises one of the peptides described above, and in particular in that it contains, in addition, amino acids which are preferably basic at the N-terminal end and/or at the C-terminal end of this peptide, and permitting amidation of the C-terminal structure thus formed of the polypeptide.

As an example, the above polypeptide can correspond to one of the peptides described previously, to which amino acids such as lysine or arginine or alternatively glycine have been added at the $NH_2$-terminal end. At the COOH end of the polypeptide, it is possible to insert an amino acid such as glycine capable of bringing about amidation of the polypeptide and lysine or arginine.

Another modification which may be envisaged consists in synthesizing cyclic analogues of the peptides described above by introducing, for example, cysteine residues into the chosen peptide, where appropriate obtained synthetically, so as to stiffen the peptide structure according to a particular spatial conformation. In this case, the linkage of amino acids whose sequence has been described above can, for example, be modified by introduction of cysteine residues introduced at positions 2 and 5 or at positions 3 and 6 in the sequence.

Another modification which may be envisaged, with the object of avoiding oxidation of the COOH-terminal methionine residue, would consist in replacing it by an norleucine residue.

A polypeptide according to the invention can also be characterized in that it is an oligomer or a polymer of one of the above peptides, or an oligomer composed of different peptides among those defined above, linked via peptide bonds.

To carry out the oligomerisation, it is possible to have recourse to any polymerisation technique commonly used in the peptide field, this polymerisation being carried out until an oligomer or polymer containing the requisite number of monomer units (the monomer consisting, in this instance, of the peptide corresponding to the above formula) for acquisition of the desired antigenicity or immunogenicity is obtained.

One method of oligomerisation or polymerisation of the monomer consists in reaction of the latter with a crosslinking agent such as glutaraldehyde.

It is also possible to have recourse to other methods of oligomerisation or coupling, for example to those involving successive couplings of monomer units, through their carboxyl and amine terminal functions, in the presence of homo- or heterobifunctional coupling agents.

It is also possible, for the production of molecules containing one or more peptide units as defined above, to have recourse to genetic engineering techniques employing microorganisms transformed by a particular nucleic acid comprising corresponding suitable nucleotide sequences.

Depending on the applications for which the peptides according to the invention are intended, it is also possible to envisage intercalating between several amino acids, or even between all the amino acids, of the peptides defined above, dextrorotatory amino acids, and in particular dextrorotatory phenylalanine or dextrorotatory tryptophan, capable of preventing the action of the degradative enzymes in the cell environment and thus of increasing their activity. Another modification in this sense consists in replacing certain amino acids, for example of the proline type, by D-tryptophan.

It is, moreover, understood that the amide group of ranakinin may be substituted, for example, monosubstituted with alkyl, aralkyl or aryl groups, or completely substituted by an ester or nitrile radical.

The modifications made to the peptides of the invention may be carried out in such a way that the peptides or polypeptides thus produced are recognized by polyclonal or monoclonal antibodies recognizing ranakinin.

Since ranakinin has so-called substance P-like activity, inasmuch as it is recognized by antibodies directed towards the COOH-terminal portion of substance P, it is also possible to define a group of peptides and polypeptides or oligomers of the latter, modified relative to ranakinin and defined by their capacity for being recognized by antibodies directed towards the COOH terminal portion of substance P.

Within the context thus specified, the different substitutions or modifications of the peptides and polypeptides of the invention must be envisaged according to the applications for which it is desired to use these compounds. In effect, when a peptide having the peptide skeleton of ranakinin is elongaate at its N-terminal end or at its COOH-terminal end, this peptide can become less accessible to an in vivo receptor. Similarly, its viscosity can increase and can consequently cause a decrease in its bioavailability.

On the other hand, if it is sought to obtain an antagonist of the peptide of the invention or to decrease its activity of binding to a receptor while increasing its antigenicity, it will be highly advisable to carry out substitutions on the parent peptide or to graft amino acid residues at the $NH_2$-and/or COOH-terminal ends.

A particular problem linked to the use of neuropeptides, in particular as therapeutic agents, stems from their inability to cross the blood-brain barrier.

The peptides of the invention may hence be used as a research tool in pharmacological models in order to determine what conformations might be likely to mimic the structure of the peptides of the invention and be capable of crossing the blood-brain barrier. In this connection, the invention relates to a molecule, peptide or otherwise, synthetic or natural, having a conformation in aqueous solution resembling that of ranakinin in its natural form, or resembling that of its derivatives corresponding to the definitions of the invention, this molecule having a rigid, non-hydrolysable structure capable of crossing the blood-brain barrier.

The peptides defined above, labelled radioactively, for example by substitution of carbon and/or hydrogen atoms by radioactive atoms, or alternatively by addition of an arm such as the Bolton-Hunter reagent grafted onto a free amine function (BOLTON and HUNTER, Biochem. J. 133, 529–538, 1973) also fall within the scope of the invention.

The invention also relates to polyclonal or monoclonal antibodies, characterized in that they specifically recognise a peptide or a polypeptide according to any one of the above definitions. An antibody possesses the capacity to recognise specifically one of the peptides or polypeptides of the invention provided it enables an antigen-antibody type reaction to be carried out and a complex to be formed with these peptides and polypeptides. A subgroup of antibodies satisfying the above conditions is further defined in that these antibodies do not recognise either the $NH_2$-terminal portion of substance P or the $NH_2$-terminal portion of neurokinin B.

The invention also relates to the antigen antibody complex in which the antigen corresponds to a peptide according to the invention, the antibody being specific for this peptide or for the group of peptides according to the invention.

The monoclonal antibodies may be obtained by conventional techniques for preparing monoclonal antibodies. The technique of fusion of myeloma cells with spleen cells of an animal (for example a mouse) immunized beforehand with ranakinin or a derivative of this peptide as defined above will generally be employed. The hybridomas resulting from the fusion of the above cells are cultured, and the antibodies which they produce are tested to select those which recognise ranakinin and, where appropriate, in this group, those which are specific for the latter under the conditions corresponding to the above definition.

According to a variant, these monoclonal antibodies can also be produced in ascites in animals.

Different applications of the peptides described above may be envisaged, stemming from the fact that they can be used as an analogue of certain neuropeptide molecules and, in particular, in the case of ranakinin, as a substance P analogue.

The invention relates, in addition, to a nucleic acid, characterized in that it codes for a peptide or polypeptide corresponding to the definitions given on the previous pages, and especially a nucleic acid corresponding to the following sequence:

AAR CCN AAY CCN GAR MGN UUY UAY
GGN YUN AUG (Seq. ID NO. 1).

There also falls within the scope of the invention a cloning and/or expression vector, characterized in that it is modified with a nucleic acid defined above at a site which is non-essential for its replication, this nucleic acid being placed under the control of regulatory elements, and in particular of a promoter recognized by the polymerases of a cell host in which it is desired to clone or express it. The invention also relates to a cell host, characterized in that it is transformed by a vector described above.

As an example of cell hosts which are especially advantageous for carrying out the invention, there are E. coli and eukaryotic cells.

It is possible, in particular, to use the cloning vector ZAP, which by itself combines many of the advantages possessed by other insertion vectors, the vector being modified with the sequence of the invention: apart from the property of being converted in vivo into plasmid Bluescript SK, it permits rapid sequencing of the nucleic acid, riboprobe production, directed mutagenesis and the expression of fusion proteins. E. coli strain BB4 is especially recommended for the propagation of ZAP. Other cloning vectors and host cells which are of interest in the context of the invention are listed in the work Molecular Cloning by Maniatis et al. (1989).

The invention also relates advantageously to the eukaryotic cells transfected by the nucleotide sequence defined above under the control of a eukaryotic gene promoter (for example the promoter of the metallothionein gene, inducible with cadmium).

The peptides according to the invention may be purified from extracts of the brain of frogs such as Rana ridibunda, or alternatively be prepared by conventional techniques in the field of peptide synthesis. This synthesis may be carried out in homogeneous solution or on a solid phase.

For example, the technique of synthesis in homogeneous solution described by HOUBEN-WEYL in the work entitled "Methoden der Organischen Chemie" [Methods in Organic Chemistry] edited by E. Wunsch, Vol. 15-I and II, THIEME, Stuttgart 1974, may be employed.

This method of synthesis consists in condensing the successive aminoacyl residues successively in pairs in the requisite order, or in condensing aminoacyl residues and fragments so prepared beforehand, on the understanding that care will have been taken to protect beforehand all the reactive groups carried by these aminoacyl residues or fragments, with the exception of the amine functions of one and the carboxyl functions of the other, or vice versa, which are normally to participate in the formation of the peptide bonds, in particular after activation of the carboxyl function, according to methods well known in peptide synthesis. As a variant, coupling reactions employing conventional coupling reagents of the carbodiimide type, for example, 1-ethyl-3-(3-dimethylaminopropyl) carbodiimide, may be employed. When the aminoacyl residue employed possesses an additional acidic function (in particular in the case of glutamic acid, these functions will, for example, be protected with t-butyl ester groups.

In the case of progressive synthesis, amino acid by amino acid, the synthesis preferably begins with the condensation of the C-terminal amino acid with the amino acid corresponding to the neighboring aminoacyl residue in the desired sequence, and so on, stepwise, up to the N-terminal amino acid. According to another preferred technique of the invention, that described by R. D. MERRIFIELD in the paper entitled "Solid phase peptide synthesis" (J. Am. Soc., 45, 2149–2154) is employed.

To manufacture a peptide chain according to MER-RIFIELD's method, a highly porous polymeric resin is employed, to which the first C-terminal amino acid of the chain is bound. This amino acid is bound to the resin via its carboxyl group, and its amine function is protected, for example with a t-butyloxycarbonyl group.

When the first C-terminal amino acid is bound in this manner to the resin, the group protecting the amine function is removed by washing the resin with an acid.

In the case where the group protecting the amine function is a t-butyloxycarbonyl group, it may be removed by treating the resin using trifluoroacetic acid.

The second amino acid which provides the second aminoacyl residue of the desired sequence, starting from the C-terminal aminoacyl residue, is then coupled onto the deprotected amine function of the first C-terminal amino acid bound to the chain. Preferably, the carboxyl function of this second amino acid is activated, for example with dicyclohexylcarbodiimide, and the amine function is protected, for example with t-butyloxycarbonyl.

The first portion of the desired peptide chain, which contains two amino acids and in which the terminal amine function is protected, is thereby obtained. As before, the amine function is deprotected and it is then possible to carry out the binding of the third aminoacyl residue, under conditions similar to those for the addition of the second C-terminal amino acid.

The amino acids which will make up the peptide chain are thus bound, one after another, to the amine group, each time deprotected beforehand, of the portion the peptide chain already formed, and which is attached to the resin.

When the whole of the desired peptide chain has been formed, the groups protecting the different amino acids making up the peptide chain are removed and the peptide is detached from the resin, for example using hydrofluoric acid.

The following examples are offered to illustrate but not limit the invention.

EXAMPLES

Material and Methods

The synthetic peptides come from Peninsula Laboratories, Inc (Belmont Cailf., USA). Chromatography columns were supplied by Separations Group (Hesperia, Cailf., USA) The FAB (fast atom bombardment) technique coupled to mass spectrometry was carried out by the Mid-West Center for mass spectrography, Chemistry Department, University of Nebraska, Lincoln, Nebr. USA.

Tissue extraction

Adult frogs (Rana ridibunda) were bought from the company Couetard, Saint-Hilaire de Riez, France. Whole brains were extracted from approximately 600 specimens and frozen immediately in dry ice. The tissue (46.7 g) was extracted when already frozen with 8 volumes of ethanol/0.7M HCl (3:1, vol/vol), as described by CONLON et al. 1986 (FEBS Lett. 200, 111–116). After stirring for 3 hours at 4° C., the extract was centrifuged (1600 g for 1 hour at 4° C.) and the ethanol was recovered from the supernatant under reduced-pressure conditions. The peptide material was isolated by passage at a flow rate of 1 ml/min through 10 Sep-Pak C-18 cartridges (Waters Associates, Milford, Mass., USA) connected in series. The bound material was recovered by elution with 70% (vol/vol) acetonitrile/water and lyophilised.

Radioimmunoassayv (RIA) protocols

Substance P-like immunoreactivity (SP-LI) was measured using a P-4 antiserum directed towards the COOH-terminal region of substance P which exhibited a reactivity of less than 0.5% with neurokinin A, neurokinin B and the unamidated form of substance P. The detection limit of the test is 4 fmol/tube. SP-LI was also measured using an SPG-1 antiserum directed towards the $NH_2$-terminal region of substance P which did not exhibit reactivity with the other tachykinins. The detection limit of the test is 0.9 fmol/tube. Neurokinin B-like immunoreactivity (NKB-LI) was measured using an R5 antiserum directed towards the $NH_2$-terminal region of neurokinin B which does not exhibit reactivity with the other tachykinins. The detection limit of the test is 6 fmol/tube. Full details of the radioimmunoassay protocols have been described in several recent articles (CONLON, 1991a, Methods in Neurosciences 6, 207–221; CONLON, 1991b, Methods in Neurosciences 6, 221–231).

Prification of ranakinin and neurokinin B by HPLC

The brain extract, after partial purification on Sep-Pak cartridges, was injected onto a Vydac 218TP510 (C-18) column (25×1 cm) equilibrated with 0.1% (vol/vol) trifluoroacetic acid/water and with a flow rate of 2 ml/min. The acetonitrile concentration was raised to 21% (vol/vol) during 10 min, maintained at this concentration for 40 min and increased to 49% (vol/vol) during 60 minutes using a linear gradient. The absorption was measured at 214 and 280 nm and the fractions (1 min) were collected. The SP-LI and NKB-LI activities in these fractions were measured by radioimmunoassays at a suitable dilution.

The fractions containing substance P-like activity (SP-Li) (FIG. 1) were combined and injected onto a Vydac 214TP54 (C-4) column (25×0.46 cm) equilibrated with 0.1% (vol/vol) trifluoroacetic acid/water with a flow rate of 1.5 ml/min. The acetonitrile concentration in the elution solvent was increased to 14.5% (vol/vol) during 10 minutes and to 35% (vol/vol) during 60 minutes using linear gradients. The ranakinin was purified to apparent homogeneity on a Vydac 218TP54 (C-18) column (25×0.46 cm) equilibrated with acetonitrile/water/trifluoroacetic acid (17.5:82.4:0.1, vol/vol/vol) with a flow rate of 1.5 ml/min. The acetonitrile concentration in the elution solvent was increased to 31.5% during 60 minutes using a linear gradient.

The fractions containing NKB-LI (FIG. 1) were collected and injected onto a Vydac 214TP54 column (25×0.46 cm) equilibrated with 0.1% (vol/vol) trifluoroacetic acid with a flow rate of 1.5 ml/min. The acetonitrile concentration in the elution solvent was adjusted to 24.5% (vol/vol) during 10 minutes and 38.5% (vol/vol) during 60 minutes. The frog neurokinin B was purified to apparent homogeneity on a Vydac 218TP54 column (25×0.46 cm) as described above, except for the fact that the acetonitrile concentration was raised from 24.5% (vol/vol) to 35% (vol/vol) during 60 minutes.

Structural characterization

The primary structure of the peptides was determined by automated Edman degradation, using an Applied Biosystems 471A sequencer modified to carry out continuous detection of phenylthiohydantoin amino acids under elution gradient conditions. The detection limit was 0.5 pmol. The amino acid compositions were determined after hydrolysis in the gaseous phase (6M HCl), by derivatisation on emergence from the column with phenyl isothiocyanate (BIDLINGMEYER et al., 1984, J. Chromatog. 336, 93–104) using an Applied Biosystems 420A derivatiser. The phenylthiocarbamyl derivatives of the amino acids were identified by HPLC using the Applied Biosystems separating system 130A. Californium-252 plasma desorption mass spectrometry was performed using a BIOION Nordic BIN-20K "time-of-flight" instrument. The spectra were recorded at 16 kV during $10^6$ primary fission events. The accuracy of the mass determinations is ±0.1%.

Synthesis of ranakinin

Ranakinin was synthesized (0.4 mmol scale) on a para-methylbenzhydrylamine resin using an Applied Biosystems 430A peptide synthesizer. Tert-Butyloxycarbonyl-protected amino acid derivatives were coupled on the basis of their hydroxybenzotriazole active esters following the manufacturer's standard protocols. The peptide was cleaved from the resin using a mixture of trifluoromethanesulphonic acid and trifluoroacetic acid (1:9, vol/vol) and purified by reversed-phase HPLC. The final concentration of purified peptide was 19% of the theoretical quantity. The identity of the peptide was confirmed by amino acid analysis (found: Asx 1.0, Glx 1.0, Gly 1.0, Arg 1.0, Pro 2.1, Tyr 0.9, Met 1.0, Leu 1.0, Phe 0.9, Lys 1.1 residues/mol peptide), and by low resolution mass spectrometry (observed mass 1353; mass calculated for the diprotonated form 1353).

RESULTS

Tachykinin-like immunoreactivity in frog's brain

The concentration of SP-LI in the extract of frog's brain, measured with an antiserum directed towards the COOH-terminal portion of substance P, was 236 pmol/g per weight of fresh tissue. SP-LI was not detectable in the extract using an antiserum directed towards the NH2-terminal portion of substance P. NKB-LI in the extract, measured with an antiserum directed towards the NH2-terminal end of neurokinin B, was 164 pmol/g of fresh tissue. The displacement curves observed with the brain extracts are parallel to the standard curves obtained with synthetic substance P and neurokinin B, respectively, in the radioimmunoassays.

Purification of ranakinin and of neurokinin B

Figure 1:
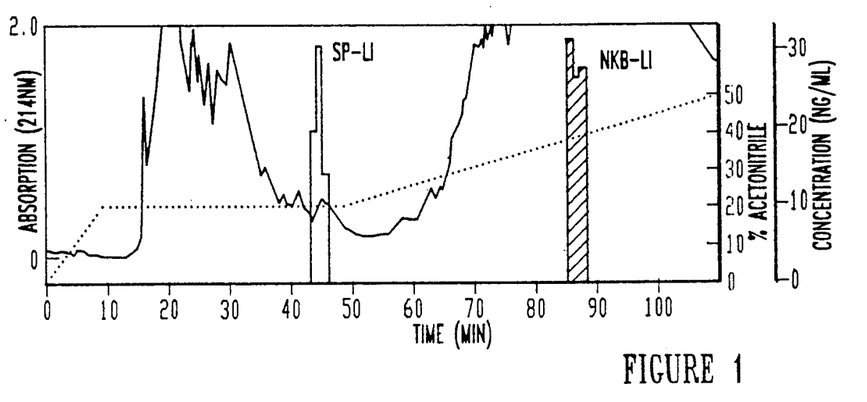
FIG. 1 shows results of reversed-phase HPLC electrophoresis on a Vydac C-18 semi-preparative column with an extract of frog brain after partial purification on Sep-Pak cartridges. The fractions indicated by the clear areas contained substance P-like immunoreactivity (SP-LI) and the fractions indicated by hatched area contained neurokinin B-like immunoreactivity (NKB-LI). The dotted line shows the concentration of acetonitrile in the elution solvent.
Figure 2A:
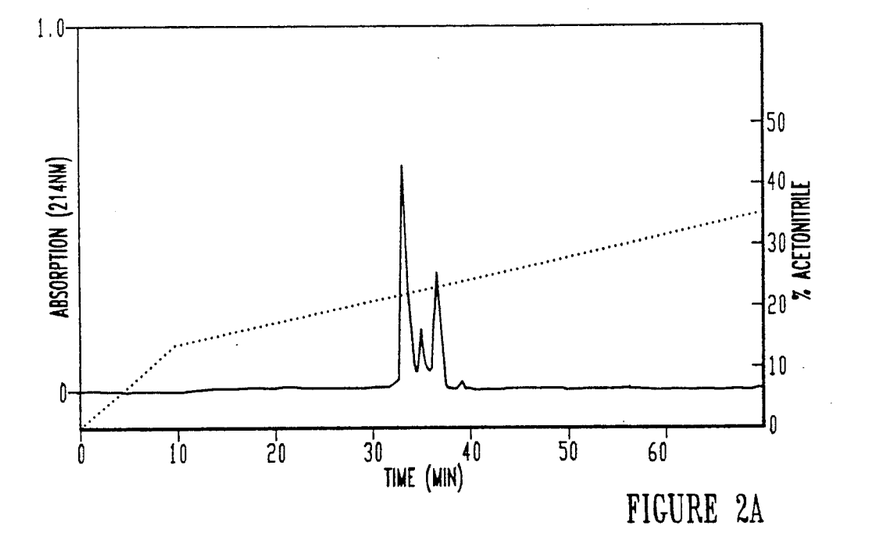
FIGS. 2A-2B shows purification of ranakinin to apparent homogeneity by chromatography on (A) a Vydac C-4 analytical column and (B) a C-18 analytical column. The peak underlined with a stroke corresponds to substance P-like immunoreactivity. The arrow indicates the retention time of substance P.
Figure 2B:
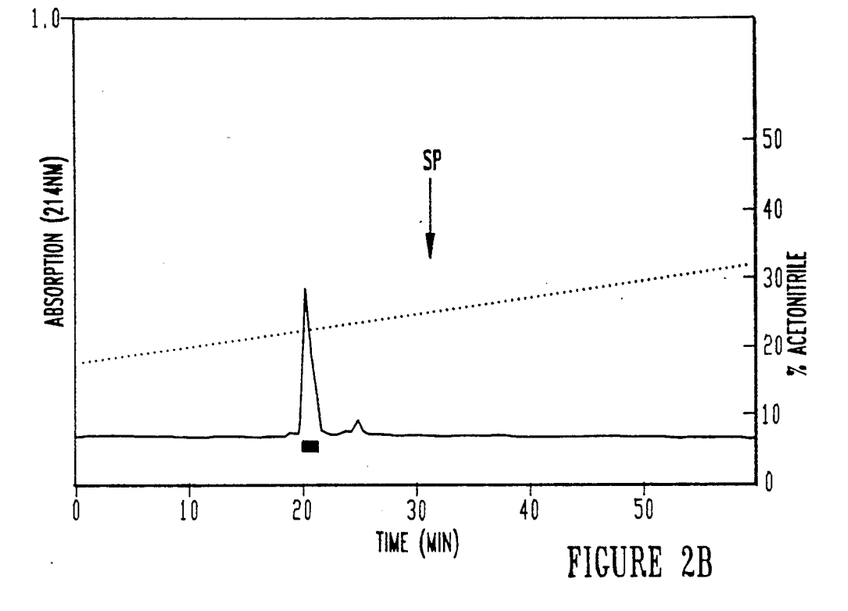

The elution profile on a semi-preparative C-18 reversed-phase HPLC column of the extract of frog's brain is shown in FIG. 1. Substance P-like activity, measured with an antiserum directed towards the COOH-terminal portion, was eluted in the form of a single peak in the fractions, and represented by a clear area. Neurokinin B-like activity, measured with an antiserum directed towards the NH2-terminal portion, was eluted in the form of a single peak in the fractions represented by a hatched area. The fractions containing SP-LI were combined and rechromatographed on a C-4 analytical column (FIG. 2A). The substance P-like activity was eluted in the form of the principal peak, indicated by a stroke. The ranakinin was purified to apparent homogeneity on a C-18 analytical column (FIG. 2B). The peptide was eluted in the form of a sharp and symmetrical peak with a retention time markedly lower than that of substance P. The final concentration of pure material was approximately 5 nmol.

Figure 3A:
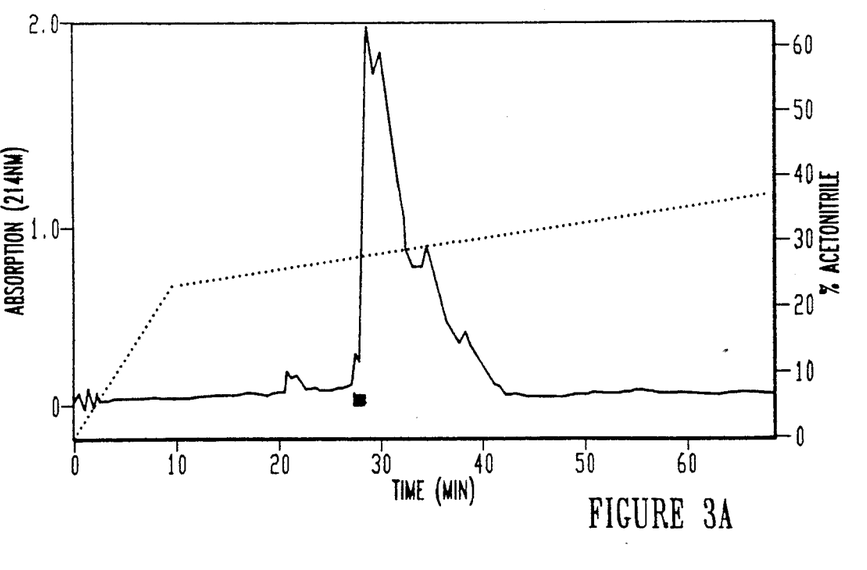
FIGS. 3A-3B shows purification of frog neurokinin B to apparent homogeneity by chromatography on (A) a Vydac C-4 analytical column and (B) a Vydac C-18 analytical column. The stroke shows the fractions containing neurokinin B-like immunoreactivity. The arrow gives the retention time of neurokinin B.
Figure 3B:
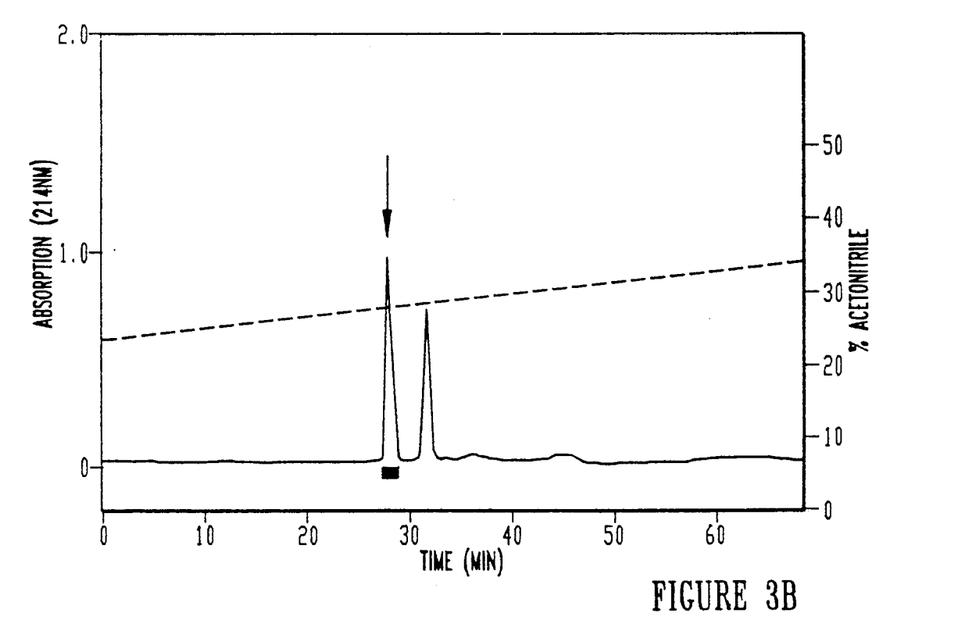

The fractions containing NKB-LI were combined and rechromatographed on a C-4 analytical column (FIG. 3A). The immunoreactivity was associated with a shoulder of the elution peak which elutes earlier than the major UV absorption peak, as shown by the stroke. After rechromatography of this fraction on a C-18 analytical column (FIG. 3B), the peptide was eluted in the form of a peak without a shoulder with the same retention time as neurokinin B. The final concentration of purified neurokinin B in the frog was approximately 2 nmol.

Structural analysis

The amino acid analysis of ranakinin revealed the following composition: Asx 1.1, Glx 1.4, Gly 1.0, Arg 1.1, Pro 1.8, Tyr 0.8, Met 0.8, Leu 1.1, Phe 0.9, Lys 0.9 (residues/mol peptide). The sequence obtained by Edman degradation is given in Table 1 below:

TABLE 1

| | Automated Edman degradation of frog ranakinin and neurokinin B | | | |
|---|---|---|---|---|
| | Ranakinin | | Neurokinin B | |
| Cycle No. | Amino acid | Quantity | Amino acid | Quantity |
| 1 | Lys | 1606 | Asp | 193 |
| 2 | Pro | 1326 | Met | 305 |
| 3 | Asn | 707 | His | 159 |
| 4 | Pro | 1001 | Asp | 122 |
| 5 | Glu | 689 | Phe | 250 |
| 6 | Arg | 560 | Phe | 185 |
| 7 | Phe | 947 | Val | 126 |
| 8 | Tyr | 885 | Gly | 81 |
| 9 | Gly | 566 | Leu | 27 |
| 10 | Leu | 201 | Met | 9 |
| 11 | Met | 66 | | |

The phenylthiohydantoin amino acids were identified unambiguously during 11 reaction cycles. The proposed amino acid sequence was in agreement with the data on the amino acid composition, demonstrating that the complete sequence of the peptide had been obtained. The observed molecular mass of the peptide, determined by plasma desorption mass spectrometry, was 1366.6±1.4, compared with the calculated mass for the proposed sequence of 1350.6. The difference of 16 amu suggests that the COOH-terminal methionine residue was oxidized to its sulphoxide form. In a previous study (CONLON et al. 1991), the observed mass of fish tachykinin, karassin, was also 16 amu larger than the calculated mass. The presence of an a-amidated COOH-terminal residue in ranakinin was suggested by the high reactivity of the peptide with the antiserum directed towards the COOH-terminal portion of substance P, and was confirmed by total synthesis. A mixture of endogenous ranakinin and a-amidated synthetic peptide was eluted from the reversed-phase HPLC column under the elution conditions shown in FIG. 2B in the form of a single peak without a shoulder.

The amino acid analysis of frog neurokinin B revealed the following composition: Asx 2.1, Gly 1.3, His 0.9, Val 1.0, Met 1.1, Leu 1.0, Phe 1.7 (residues/mol peptide). With the exception of the low value for methionine in the composition, the composition of the frog peptide is the same as that expected for mammalian neurokinin B. The identity of frog neurokinin B with mammalian neurokinin B was confirmed by Edman degradation (Table 1) and a mixture of the endogenous peptide and the synthetic neurokinin B eluted from the C-18 reversed-phase HPLC column in the form of a single peak. The observed molecular mass of frog neurokinin B was $1209.7 \pm 1.2$, which is in agreement with the calculated mass of 1210.4 for the alpha-amidated form of the proposed sequence.

---

What is claimed is:

1. A peptide, characterized in that it corresponds to the following sequence of amino acids:

Lys Pro Asn Pro Glu Arg Phe Tyr Gly Leu Met.

2. A peptide of claim 1 characterized in that its COOH-terminal end is amidated.

3. A polypeptide containing from about 30 to about 40 amino acid residues and characterized in that it comprises the peptide according to claim 1 and contains, in addition, basic amino acids at the N-terminal end and/or at the C-terminal end, and if at the C-terminal end, said C-terminal structure is one which permits amidation of the polypeptide.

4. A method of preparing a peptide comprising:
  (a) centrifuging of a frog brain tissue extract;
  (b) separating of the peptide fraction;
  (c) selecting the peptide fraction reacting with an antiserum in which the polyclonal or monoclonal antibodies recognise the COOH-terminal portion of substance P, said antiserum exhibiting, a reactivity of less than 0.5% with neurokinin A, neurokinin B and unamidated substance P;
  (d) purifying said peptide fraction; and
  (e) recovering said purified peptide.

5. A peptide according to claim 1 having intercalated between some of the amino acids of the peptide, dextrorotary amino acids.

6. A peptide according to claim 2, characterized in that the $NH_2$ group is substituted with a moiety selected from the group alkyl, aralkyl, aryl, ester, and nitrile.

7. Monoclonal or polyclonal antibodies, characterized in that they specifically recognise a peptide or a polypeptide according to claim 1.

* * * * *